(12) United States Patent
Liu et al.

(10) Patent No.: US 6,472,545 B2
(45) Date of Patent: Oct. 29, 2002

(54) PROTEIN TYROSINE PHOSPHATASE INHIBITORS

(75) Inventors: Gang Liu, Gurnee, IL (US); Zhonghua Pei, Libertyville, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/935,992

(22) Filed: Aug. 23, 2001

(65) Prior Publication Data

US 2002/0077347 A1 Jun. 20, 2002

Related U.S. Application Data

(60) Provisional application No. 60/228,652, filed on Aug. 29, 2000.

(51) Int. Cl.[7] .................. C07D 307/91; C07D 317/48
(52) U.S. Cl. ........................... 549/461; 549/434
(58) Field of Search ................... 549/461, 434

(56) References Cited

FOREIGN PATENT DOCUMENTS

| EP | 0455006 | 11/1991 |
|----|---------|---------|
| WO | 99 46236 | 9/1999 |
| WO | 99 46267 | 9/1999 |
| WO | 99 46268 | 9/1999 |
| WO | 99 58518 | 11/1999 |
| WO | 99 61410 | 12/1999 |
| WO | 99 61435 | 12/1999 |

OTHER PUBLICATIONS

Wrobel et al. PTP1B Inhibition and Antihyperglycemic Activity in the ob/ob Mouse Model of Novel 11–Arylbenzo[b]naphtha[2,3–d]furans and 11–Arylbenzo[b]naphtha[2,3–d]thiophenes, J. of Med. Chem. 1999, Am. Chem. Soc., vol. 42, No. 17, pp. 3199–3202.*

Malamas, M.S. et al, "Novel Benzofuran and Benzothiophene Biphenyls as Inhibitors of Protein Tyrosine Phosphatase 1B with Antihyperglycemic Properties", Journal of Medicinal Chemistry (2000) 43: 1293–1310, XP002190818.

* cited by examiner

*Primary Examiner*—Deborah C. Lambkin
*Assistant Examiner*—Sameena Ahmed
(74) *Attorney, Agent, or Firm*—Daniel W. Collins

(57) ABSTRACT

Compounds of formula (I)

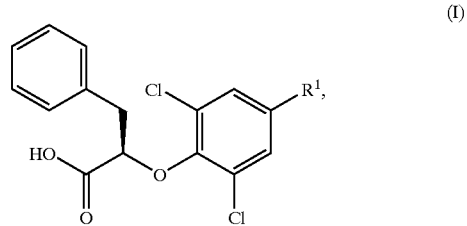

or therapeutically acceptable salts thereof, are protein tyrosine kinase PTP1B inhibitors. Preparation of the compounds, compositions containing the compounds, and treatment of diseases using the compounds are disclosed.

10 Claims, No Drawings

PROTEIN TYROSINE PHOSPHATASE INHIBITORS

This application claims priority to the provisional application Serial No. 60/228,652 filed on Aug. 29, 2000.

TECHNICAL FIELD

The instant invention is directed to compounds useful for inhibiting protein tyrosine phosphatase PTP1B, preparation of the compounds, compositions containing the compounds, and treatment of diseases using the compounds.

BACKGROUND OF THE INVENTION

PTP1B belongs to a family of protein tyrosine phosphatases involved in the regulation of the cellular signaling mechanisms which are involved in metabolism, growth, proliferation, and differentiation (*Science* 253:401–6 (1991)). Overexpression or altered activity of tyrosine phosphatase PTP1B can contribute to the progression of various diseases (*Ann. Rev. Biochem.*, 54:897–930 (1985)); and there is evidence which suggests inhibition of protein tyrosine phosphatase PTP1B is therapeutically beneficial for the treatment of diseases such as type I and II diabetes, obesity, autoimmune disease, acute and chronic inflammation, osteoporosis, and various forms of cancer (*J. Natl. Cancer Inst.* 86:372–8 (1994); *Mol. Cell. Biol.* 14: 6674–6682 (1994); *The EMBO J.* 12:1937–46 (1993); *J. Biol. Chem.* 269:30659–30667 (1994); and *Biochemical Pharmacology* 54:703–711 (1997)).

Because of the important role played by unregulated protein tyrosine phosphatase PTP1B in these diseases, agents which inhibit the enzyme have been the subject of active current research for their clinical potential. Reference is made to WO 99/46236, WO 99/46237, WO 99/46267 and WO 99/46268; and although each teaches protein tyrosine phosphatase PTP1B inhibitors, there is still a need for protein tyrosine phosphatase PTP1B inhibitors with modified or improved profiles of activity.

SUMMARY OF THE INVENTION

In its principle embodiment, therefore, the instant invention provides compounds of formula (I)

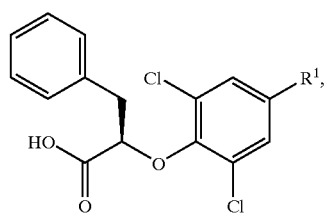

(I)

or therapeutically acceptable salts thereof, wherein
$R^1$ is selected from the group consisting of benzodioxolyl, dibenzofuranyl, indolyl, phenyl, and thianthrenyl;
wherein the benzodioxolyl, the dibenzofuranyl, the indolyl, and the thianthrenyl can be optionally substituted with one, two, three, or four substituents independently selected from the group consisting of alkanoyl, alkoxy, alkoxycarbonyl, alkyl, amino, aryl, arylalkyl, carbonyloxy, carboxy, cyano, cycloalkyl, cycloalkylalkyl, halo, hydroxy, hydroxyalkyl, nitro, perfluoroalkoxy, perfluoroalkyl, and thioalkoxy; and
wherein the phenyl is substituted with one, two, three, or four substituents independently selected from the group consisting of perfluoroalkoxy and phenyl.

In still another embodiment the instant invention provides a method for inhibiting protein tyrosine phosphatase comprising administering a therapeutically effective amount of a compound of formula (I).

In still another embodiment the instant invention provides a method for treating diseases in a patient in recognized need of such treatment comprising administering to the patient a therapeutically effective amount of a compound of formula (I).

In still another embodiment the instant invention provides a composition comprising a compound of formula (I) in combination with a therapeutically acceptable excipient.

DETAILED DESCRIPTION OF THE INVENTION

The instant invention provides a series of compounds which inhibit protein tyrosine phosphatase PTP1B. As used throughout the specification of the instant invention, the following terms, as used herein, have the meanings indicated:

The term "alkanoyl," as used herein, represents an alkyl group attached to the parent molecular moiety through a carbonyl group.

The term "alkoxy," as used herein, represents an alkyl group attached to the parent molecular moiety through an oxygen atom.

The term "alkoxycarbonyl," as used herein, represents an alkoxy group attached to the parent molecular moiety through a carbonyl group.

The term "alkyl," as used herein, represents a saturated, monovalent straight or branched chain hydrocarbon having from one to six carbons.

The term "amino," as used herein, represents —$NR^2R^3$, wherein $R^2$ and $R^3$ are independently selected from the group consisting of hydrogen, alkanoyl, alkoxycarbonyl, alkyl, cycloalkyl, cycloalkylalkyl, a nitrogen protecting group, phenyl, and phenylalkyl; or $R^2$ and $R^3$, together with the nitrogen atom to which they are attached, form a ring selected from the group consisting of morpholinyl, oxazinanyl, piperazinyl, piperidinyl, and pyrrolidinyl.

The term "aryl," as used herein, represents dihydronaphthyl, indanyl, indenyl, naphthyl, phenyl, and tetrahydronaphthyl. Aryl groups having an unsaturated or partially saturated ring fused to an aromatic ring can be attached through the saturated or the unsaturated part of the group.

The term "arylalkyl," as used herein, represents an aryl group attached to the parent molecular moiety through an alkyl group.

The term "carbonyl," as used herein, represents —C(O)—.

The term "carbonyloxy," as used herein, represents an alkanoyl group attached to the parent molecular group through an oxygen atom.

The term "carboxy," as used herein, represents —$CO_2H$.

The term "cyano," as used herein, represents —CN.

The term "cycloalkyl," as used herein, represents a monovalent saturated cyclic or bicyclic hydrocarbon group of three to twelve carbons.

The term "cycloalkylalkyl," as used herein, represents a cycloalkyl group attached to the parent molecular moiety through an alkyl group.

The term "halo," as used herein, represents F, Cl, Br, or I.

The term "hydroxy," as used herein, represents —OH.

The term "hydroxyalkyl," as used herein, represents a hydroxy group attached to the parent molecular group through an alkyl group.

The term "nitro," as used herein, represents —NO$_2$.

The term "nitrogen protecting group," as used herein, represents selectively introducible and removable groups which protect amino groups against undesirable side reactions during synthetic procedures. Examples of amino protecting groups include methoxycarbonyl, ethoxycarbonyl, trichloroethoxycarbonyl, benzyloxycarbonyl (Cbz), chloroacetyl, trifluoroacetyl, phenylacetyl, formyl, acetyl, benzoyl, tert-butoxycarbonyl (Boc), para-methoxybenzyloxycarbonyl, isopropoxycarbonyl, phthaloyl, succinyl, benzyl, diphenylmethyl, triphenylmethyl (trityl), methylsulfonyl, phenylsulfonyl, para-toluenesulfonyl, trimethylsilyl, triethylsilyl, triphenylsilyl, and the like.

The term "perfluoroalkoxy," as used herein, represents a perfluoroalkyl group attached to the parent molecular moiety through an oxygen atom.

The term "perfluoralkyl," as used herein, represents an alkyl group in which all of the hydrogen atoms have been replaced with fluoride atoms.

The term "phenylalkyl," as used herein, represents a phenyl group attached to the parent molecular group through an alkyl group.

The term "thioalkoxy," as used herein, represents an alkyl group attached to the parent molecular moiety through a sulfur atom.

The instant compounds can exist as therapeutically acceptable salts. The term "therapeutically acceptable salt," refers to salts or zwitterions of the compounds which are water or oil-soluble or dispersible; suitable for treatment of diseases without undue toxicity, irritation, and allergic response; commensurate with a reasonable benefit/risk ratio; and effective for their intended use. The salts can be prepared during the final isolation and purification of the compounds or separately by reacting the amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the instant compounds by reaction the carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the instant invention.

The instant compounds can also exist as therapeutically acceptable prodrugs. The term "therapeutically acceptable prodrug," refers to those prodrugs or zwitterions which are suitable for use in contact with the tissues of patients without undue toxicity, irritation, and allergic response, are commensurate with a reasonable benefit/risk ratio, and are effective for their intended use.

The term "prodrug," refers to compounds which are rapidly transformed in vivo to parent compounds of formulas (I) and (II) for example, by hydrolysis in blood.

Asymmetric centers can exist in the instant compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Therapeutic compositions of the instant compounds comprise an effective amount of the same formulated with one or more therapeutically acceptable excipients. The term "therapeutically acceptable excipient," refers to a non-toxic, solid, semi-solid, or liquid filler, diluent, encapsulating material, or formulation auxiliary of any type. Examples of therapeutically acceptable excipients include sugars; cellulose and derivatives thereof; oils; glycols; solutions; buffering, coloring, releasing, coating, sweetening, flavoring, and perfuming agents; and the like. These therapeutic compositions can be administered parenterally, intracisternally, orally, rectally, or intraperitoneally.

Liquid dosage forms for oral administration of the instant compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents.

Injectable preparations of the instant compounds comprise sterile, injectable, aqueous and oleaginous solutions, suspensions, or emulsions, any of which can be optionally formulated with parenterally acceptable diluents, dispersing, wetting, or suspending agents. These injectable preparations can be sterilized by filtration through a bacterial-retaining filter or formulated with sterilizing agents which dissolve or disperse in the injectable media.

PTP inhibition by the instant compounds can be delayed by using a liquid suspension of crystalline or amorphous material with poor water solubility. The rate of absorption of the compounds depends upon their rate of dissolution which, in turn, depends on their crystallinity. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the instant compounds include capsules, tablets, pills, powders, and granules. In such forms, the compound is mixed with at least one inert, therapeutically acceptable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The instant compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the instant compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Diseases caused or exacerbated by protein tyrosine phosphatase PTP 1B activity are treated or prevented in a patient by administering to the same a therapeutically effective amount of the instant compounds in such an amount and for such time as is necessary to achieve the desired result. The term "therapeutically effective amount," refers to a sufficient amount of the compound to treat protein tyrosine phosphatase PTP1B activity at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the instant compounds in single or divided doses can be in amounts, for example, from 0.01 to 50 mg/kg body weight or more usually from 0.1 to 25 mg/kg body weight. Single dose compositions can contain such amounts or submultiples thereof of the compounds to make up the daily dose. In general, treatment regimens comprise administration to a patient in need of such treatment from about 10 mg to about 1000 mg of the compounds per day in single or multiple doses.

Specific compounds of the invention include, but are not limited to, (2R)-2-(2,6-dichloro-4-dibenzo(b,d)furan-4-ylphenoxy)-3-phenylpropanoic acid; (2R)-2-((3,5-dichloro-4'-(trifluoromethoxy)(1,1'-biphenyl)-4-yl)oxy)-3-phenylpropanoic acid; (2R)-2-((3,5-dichloro-3'-phenyl(1,1'-biphenyl)-4-yl)oxy)-3-phenylpropanoic acid; (2R)-2-(2,6-dichloro-4-(1H-indol-5-yl)phenoxy)-3-phenylpropanoic acid; (2R)-2-(2,6-dichloro-4-(1-thianthrenyl)phenoxy)-3-phenylpropanoic acid; and (2R)-2-(4-(1,3-benzodioxol-5-yl)-2,6-dichlorophenoxy)-3-phenylpropanoic acid.

Determination of Biological Activity

Purification of Human Protein Tyrosine Phosphatase 1B from *E. coli*

Human protein tyrosine phosphatase 1B (PTP1B, amino acid residues 1–321) was expressed in *E. coli* BL21(DE3). The cell paste was resuspended in 4 cell paste volumes of lysis buffer containing 100 mM MES (pH 6.5), 100 mM NaCl, 1 mM EDTA, 1 mM DTT, 1 mM PMSF, 20 U/mL Benzonase, 0.5 mg/mL lysozyme, and 1 mM $MgCl_2$ and incubated for 35 minutes at room temperature. The cells were lysed at 11,000 psi using a Rannie homogenizer, and the homogenate was clarified in a Beckman GSA rotor at 10,000×g for 30 minutes at 4° C. The supernatant was loaded onto a 5×21 cm S-Sepharose-FF column (Amersham Pharmacia Biotech) pre-equilibrated with 5 column volumes of buffer containing 100 mM MES (pH 6.5), 100 mM NaCl, 1 mM EDTA, and 1 mM DTT and eluted with 10 column volumes of the same. The fractions (28 mL each) were assayed for protein by 10–20% Tris-Glycine SDS-PAGE. Fractions which contained >95% protein tyrosine phosphatase 1B were combined.

Protein Tyrosine Phosphatase 1B Activity Assay

Protein tyrosine phosphatase 1B activity was determined by measuring the phosphate release from triphosphorylated peptide which corresponds to residues 1135–1156 of the β-subunit of the human insulin receptor (βIRK substrate) as described in *Nature*, 1985, 313, 756–761. Protein tyrosine phosphatase 1B activity was determined in a final assay volume of 50 μL containing 50 mM Tris HCl, 50 mM Tris Base, 150 mM NaCl, 3 mM DTT, 2 nM protein tyrosine phosphatase 1B(1-321), and 20 μM βIRK substrate. Various concentrations of test compounds in 5 μL of 10% DMSO were incubated for 5 minutes at room temperature in assay buffer (25 μl) containing 20 μM βIRK substrate in a round-bottom microtiter plate (Costar) pre-coated with 1% bovine serum albumin. The assay was initiated by the addition of protein tyrosine phosphatase 1B enzyme (20 μl)in assay buffer. After 10 minutes of incubation at room temperature, the reaction was terminated by the addition of 100 μL of malachite green (Upstate Biotechnology Inc.) containing 0.01% Tween-20. After a 5 minute incubation, quantitation of free phosphate released from the βIRK substrate was determined in a Victor II plate reader (Wallac; Turku, Finland) by measuring the absorbence of the malachite green at 620 nm.

The instant compounds were found to inhibit protein tyrosine phosphatase 1B with inhibitory potencies under 35 μM. As protein tyrosine phosphatase 1B inhibitors, therefore, the instant compounds are useful for treating diseases caused by overexpressed or altered protein tyrosine phosphatase 1B activity. These diseases include autoimmune diseases, acute and chronic inflammatory diseases, osteoporosis, obesity, cancer, malignant diseases, and type I and type II diabetes.

Synthetic Methods

Abbreviations which have been used in the descriptions of the scheme and the examples that follow are: DEAD for diethyl azodicarboxylate; DIAD for diisopropyl azodicarboxylate; THF for tetrahydrofuran; dba for dibenzylideneacetone; and DMSO for dimethylsulfoxide.

The compounds and processes of the instant invention will be better understood in connection with the following synthetic scheme which illustrates the methods by which the compounds of the invention may be prepared. The group $R^1$ is as defined above unless otherwise noted below.

Scheme 1

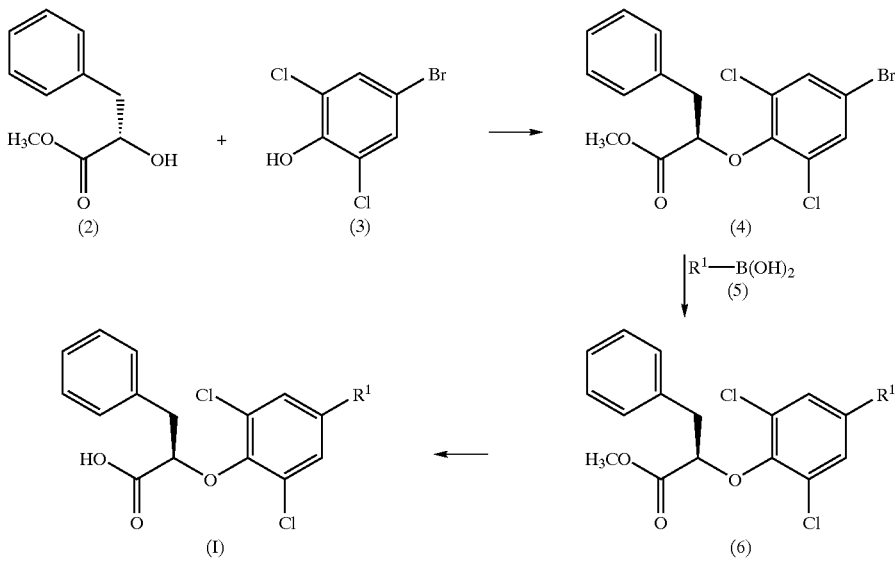

As shown in Scheme 1, compounds of formula (2) can be reacted with 4-bromo-2,6-dichlorophenol (3) in the presence of a trialkylphosphine or triarylphosphine and a diazo compound to provide compounds of formula (4). Representative trialkylphosphines include tributylphosphine and trimethylphosphine; representative triarylphosphines include triphenylphosphine and tri-o-tolylphosphine; and representative diazo compounds include DEAD and DIAD. Solvents commonly used in these reactions include THF, diethyl ether, and methyl tert-butyl ether. The reaction is conducted at about 20° C. to about 40° C., and typical reaction times are about 30 minutes to about 12 hours.

Compounds of formula (4) can be coupled to compounds of formula (5) in the presence of a palladium catalyst and base to provide compounds of formula (6). Representative palladium catalysts include $Pd(PPh_3)_4$, $PdCl_2(PPh_3)_2$, and $Pd_2(dba)_3$ with $PPh_3$. Examples of bases include CsF, $K_2CO_3$, $Na_2CO_3$, and $Cs_2CO_3$. Solvents commonly used in these reactions include toluene, benzene, and xylene. The reaction temperature about 80° C. to about 115° C., and depends on the solvent and reagents chosen. Reaction times are typically about 12 to about 24 hours.

Conversion of compounds of formula (6) to compounds of formula (I) can be accomplished under hydrolysis conditions. Representative hydrolyzing reagents include LiOH, KOH, and NaOH. Examples of solvents used in these reactions include methanol, water, tetrahydrofuran, and mixtures thereof. The reaction is conducted at about 20° C. to about 40° C., and reaction times are typically about 1 to about 6 hours.

The instant invention will now be described in connection with certain preferred embodiments which are not intended to limit its scope. On the contrary, the instant invention covers all alternatives, modifications, and equivalents as can be included within the scope of the claims. Thus, the following examples, which include preferred embodiments, will illustrate the preferred practice of the instant invention, it being understood that the examples are for the purposes of illustration of certain preferred embodiments and are presented to provide what is believed to be the most useful and readily understood description of its procedures and conceptual aspects.

EXAMPLE 1

(2R)-2-(2,6-dichloro-4-dibenzo(b,d)furan-4-ylphenoxy)-3-phenylpropanoic acid

EXAMPLE 1A methyl (2R)-2-(4-bromo-2,6-dichlorophenoxy)-3-phenylpropanoate

A solution of 4-bromo-2,6-dichlorophenol (1.24 g, 6.02 mmol), methyl (2S)-2-hydroxy-3-phenylpropanoate (1.30 g, 7.22 mmol) and triphenylphosphine (2.05 g, 7.83 mmol) in THF (13 mL) at room temperature was treated with DEAD (1.28 mL, 8.13 mmol), stirred for 2 hours, and concentrated. The concentrate was triturated with 10% ethyl acetate/hexanes, filtered, and concentrated. The concentrate was purified by flash column chromatography on silica gel with 5% ethyl acetate/hexanes to provide 1.90 g (78%) of the desired product.

EXAMPLE 1B methyl (2R)-2-(2,6-dichloro-4-dibenzo(b,d)furan-4-ylphenoxy)-3-phenylpropanoate A mixture of Example 1A (944 mg, 2.34 mmol), dibenzo(b,d)furan-4-ylboronic acid (619 mg, 2.92 mmol), $Pd(PPh_3)_4$ (216 mg, 0.187 mmol), and 2M $Na_2CO_3$ (5 mL, 10 mmol) in toluene (10 mL) was heated to 78° C., stirred for 18 hours, cooled to room temperature, and concentrated. The concentrate was purified by flash column chromatography on silica gel with 10% ethyl acetate/hexanes to provide 1.05 g (91%) of the desired product.

EXAMPLE 1C (2R)-2-(2,6-dichloro-4-dibenzo(b,d)furan-4-ylphenoxy)-3-phenylpropanoic acid A solution of Example 1B (1.03 g, 2.10 mmol) in a mixture of THF (4 mL), methanol (6 mL), and water (3 mL) at room temperature was treated with NaOH (0.42 g, 10.5 mmol), stirred for 3 hours, adjusted to pH <7 with 1N HCl, and extracted with ethyl acetate. The combined extracts were dried (Na$_2$SO$_4$), filtered, and concentrated to provide a quantitative yield of the desired product.

MS (ESI(−)) m/e 475 (M−H)$^-$;

$^1$H NMR (300 MHz, DMSO-d$_6$) δ8.21 (d, 2H), 8.02 (s, 2H), 7.82 (d, 1H), 7.77 (dd, 1H), 7.58 (dd, 1H), 7.51 (t, 2H), 7.45 (t, 1H), 7.22–7.38 (m, 4H), 5.05 (dd, 1H), 3.50 (m, 2H).

EXAMPLE 2

(2R)-2-((3,5-dichloro-4'-(trifluoromethoxy)(1,1'-biphenyl)-4-yl)oxy)-3-phenylpropanoic acid The desired product was prepared by substituting 4-trifluoromethylphenylboronic acid for dibenzo(b,d)furan-4-ylboronic acid in Example 1.

MS (ESI(−)) m/e 469 (M−H)$^-$;

$^1$H NMR (300 MHz, DMSO-d$_6$) δ7.86 (d, 2H), 7.81 (s, 2H), 7.45 (d, 2H), 7.35–7.20 (m, 3H), 4.99 (dd, 1H), 3.30 (m, 2H).

EXAMPLE 3

(2R)-2-((3,5-dichloro-3'-phenyl(1,1'-biphenyl)-4-yl)oxy)-3-phenylpropanoic acid

The desired product was prepared by substituting 3-(dihydroxyboryl)-1,1'-biphenyl for dibenzo(b,d)furan-4-ylboronic acid in Example 1.

MS (ESI(−)) m/e 461 (M−H)$^-$;

$^1$H NMR (300 MHz, DMSO-d$_6$) δ7.95 (m, 1H), 7.90 (s, 2H), 7.80 (d, 2H), 7.70 (dd, 2H), 7.56 (d, 1H), 7.54–7.38 (m, 3H), 7.37–7.20 (m, 5H), 4.99 (dd, 1H).

EXAMPLE 4

(2R)-2-(2,6-dichloro-4-(1H-indol-5-yl)phenoxy)-3-phenylpropanoic acid

The desired product was prepared by substituting 1H-indol-5-ylboronic acid for dibenzo(b,d)furan-4-ylboronic acid in Example 1.

MS (ESI(−)) m/e 424 (M−H)$^-$;

$^1$H NMR (500 MHz, DMSO-d$_6$) δ7.79 (s, 1H), 7.65–7.60 (m, 2H), 7.58–7.53 (m, 2H), 7.52 (s, 1H), 7.44 (d, 1H), 7.37 (t, 1H), 7.34 (d, 1H), 7.32 (d, 2H), 7.23 (t, 2H), 7.14 (t, 1H), 6.47 (m, 1H), 5.06 (dd, 1H), 3.50 (1H, m), 3.06 (dd, 1H).

EXAMPLE 5

(2R)-2-(2,6-dichloro-4-(1-thianthrenyl)phenoxy)-3-phenylpropanoic acid

The desired product was prepared by substituting 1-thianthrenylboronic acid for dibenzo(b,d)furan-4-ylboronic acid in Example 1.

MS (ESI(−)) m/e 523 (M−H)$^-$;

$^1$H NMR (300 MHz, DMSO-d$_6$) δ7.66 (dd, 1H), 7.61 (dd, 1H), 7.52 (s, 1H), 7.49 (dd, 1H), 7.44 (d, 1H), 7.40–7.22 (m, 8H), 5.06 (dd, 1H), 3.50 (2H, m).

EXAMPLE 6

(2R)-2-(4-(1,3-benzodioxol-5-yl)-2,6-dichlorophenoxy)-3-phenylpropanoic acid

The desired product was prepared by substituting 1,3-benzodioxol-5-ylboronic acid for dibenzo(b,d)furan-4-ylboronic acid in Example 1.

MS (ESI(−)) m/e 429 (M−H)$^-$;

$^1$H NMR (500 MHz, DMSO-d$_6$) δ7.51 (s, 1H), 7.30 (d, 2H), 7.26–7.22 (m, 3H), 7.16 (dd, 1H), 7.13 (dd, 1H), 6.96 (d, 1H), 6.05 (s, 2H), 5.00 (dd, 1H), 3.50 (1H, dd), 3.05 (dd, 1H).

It will be evident to one skilled in the art that the instant invention is not limited to the forgoing illustrative examples, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims and therefore intended to be embraced therein.

What is claimed is:

1. A compound of formula (I)

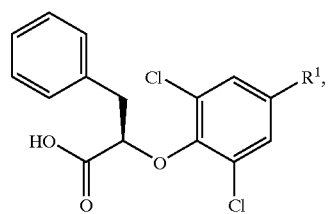

or a therapeutically acceptable salt thereof, wherein

R$^1$ is selected from the group consisting of benzodioxolyl, and dibenzofuranyl;

wherein the benzodioxolyl and the dibenzofuranyl can be optionally substituted with one, two, three, or four substituents independently selected from the group consisting of alkanoyl, alkoxy, alkoxycarbonyl, alkyl, amino, aryl, arylalkyl, carbonyloxy, carboxy, cyano, cycloalkyl, cycloalkylalkyl, halo, hydroxy, hydroxyalkyl, nitro, perfluoroalkoxy, perfluoroalkyl, and thioalkoxy.

2. A compound according to claim 1, wherein R$^1$ is benzodioxolyl.

3. A compound according to claim 2 which is (2R)-2-(4-(1,3-benzodioxol-5-yl)-2,6-dichlorophenoxy)-3-phenylpropanoic acid.

4. A compound according to claim 1, wherein R$^1$ is dibenzofuranyl.

5. A compound according to claim 4 which is (2R)-2-(2,6-dichloro-4-dibenzo(b,d)furan-4-ylphenoxy)-3-phenylpropanoic acid.

6. A method for inhibiting protein tyrosine phosphatase comprising administering a therapeutically effective amount of a compound of claim 1.

7. A method for treating diseases in a patient in recognized need of such treatment comprising administering to the patient a therapeutically effective amount of a compound of claim 1.

8. The method of claim 7 wherein the disease is selected from the group consisting of type II diabetes and obesity.

9. A composition comprising a compound of claim 1 in combination with a therapeutically acceptable excipient.

10. A compound selected from the group consisting of (2R)-2-(2,6-dichloro-4-dibenzo(b,d)furan-4-ylphenoxy)-3-phenylpropanoic acid, (2R)-2-(4-(1,3-benzodioxol-5-yl)-2,6-dichlorophenoxy)-3-phenylpropanoic acid.

* * * * *